(12) United States Patent
Fattom et al.

(10) Patent No.: US 7,754,225 B2
(45) Date of Patent: Jul. 13, 2010

(54) METHOD OF PROTECTING AGAINST STAPHYLOCOCCAL INFECTION

(75) Inventors: Ali Fattom, Rockville, MD (US); Jawad Sarwar, Germantown, MD (US); Zuzana Kossaczka, Bethesda, MD (US); Kimberly L. Taylor, Bethesda, MD (US); Sofiane Ennifar, Silver Spring, MD (US)

(73) Assignee: Glaxosmithkline Biologicals S.A., Rixensart (BE)

( * ) Notice: Subject to any disclaimer, the term of this patent is extended or adjusted under 35 U.S.C. 154(b) by 761 days.

(21) Appl. No.: 11/490,512

(22) Filed: Jul. 20, 2006

(65) Prior Publication Data
US 2008/0019983 A1    Jan. 24, 2008

(51) Int. Cl.
*A61K 39/385* (2006.01)
(52) U.S. Cl. ............ 424/243.1; 424/193.1; 424/197.11; 424/234.1
(58) Field of Classification Search ........................ None
See application file for complete search history.

(56) References Cited

U.S. PATENT DOCUMENTS

| 5,961,975 A | 10/1999 | Fattom et al. |
| 2005/0158346 A1 | 7/2005 | Kubler-Kielb et al. |

OTHER PUBLICATIONS

International Search Report and Written Opinion of the International Searching Authority dated Jul. 14, 2008, issued in PCT/US07/74010. PCT/US07/74010 claims priority from the present application.
Kubler-Kielb, et al.; "Chemical Structure, Conjugation, and Cross-Reactivity of *Bacillus pumilus* Sh18 Cell Wall Polysaccharide"; Journal of Bacteriology, Oct. 2004; vol. 186, No. 20; pp. 6891-6901.
Maira-Litran, et al.; "Biologic properties and vaccine potential of the staphylococcal poly-N-acetyl glucosamine surface polysaccharide"; Vaccine 22 (2004); pp. 872-879.
Sadovskaya, et al.; "Structural elucidation of the extracellular and cell-wall teichoic acids of Staphylococcus epidermidis RP62A, a reference biofilm-positive strain"; Carbohydrate Research 339 (2004); pp. 1467-1473.
Preliminary report on patentability issued in corresponding PCT/US07/74010, dated Jan. 20, 2009.

*Primary Examiner*—Jennifer E Graser
(74) *Attorney, Agent, or Firm*—Rossi, Kimms & McDowell LLP

(57) ABSTRACT

A method of preventing or treating staphylococcal bacterial infection in an individual is disclosed. A vaccine based on a conjugate of PS1 polysaccharide antigen can be used for active protection in individuals who are to be subjected to conditions that place them at immediate risk of developing a bacterial infection, as would be case in the context of a catheterization or a surgical procedure. Alternatively, antibodies raised in response to the antigen can be used to treat or to provide passive protection to individuals. The method can be used in a population of patients at risk for infection by various species of *Staphylococcus* or various types of *Staphylococcus epidermidis*.

11 Claims, 2 Drawing Sheets

METHOD OF PROTECTING AGAINST STAPHYLOCOCCAL INFECTION

BACKGROUND OF THE INVENTION

A. Field of the Invention

The invention relates generally to the use of staphylococcal vaccines in preventing bacterial infection in an individual.

B. Description of the Related Art

Staphylococci and Enterococci rarely cause systemic infections in otherwise healthy individuals, and therefore are considered opportunistic pathogens. Through various mechanisms, normal adult humans and animals with a competent immune system attain an innate natural resistance to these bacterial infections. These include mucosal and epidermal barriers, in addition to possible immunological mechanisms. Interruption of these natural barriers as a result of injuries such as burns, traumas, or surgical procedures involving indwelling medical devices, increases the risk for staphylococcal and enterococcal infections. In addition, individuals with a compromised immune response such as cancer patients undergoing chemotherapy and radiation therapy, diabetes, AIDS, alcoholics, drug abuse patients, post organ transplantation patients and infants are at an increased risk for staphylococcal and enterococcal infections.

Staphylococci are commensal bacteria of the anterior nares, skin, and the gastrointestinal tract of humans. It is estimated that staphylococcal infections account for >50% of all hospital acquired infections. *S. aureus* alone is responsible for 15-25% of such infections and is surpassed only by *S. epidermidis*, which accounts for 35% of these infections. Staphylococcal infections, especially those caused by *S. aureus* are associated with high morbidity and mortality.

*Staphylococcus* and *Enterococcus* are a major cause of nosocomial and community-acquired infections, including bacteremia, metastatic abscesses, septic arthritis, endocarditis, osteomyelitis, and wound infections. For example, the bacteremia-associated overall mortality for *S. aureus* is approximately 25 percent. A study of hospitalized patients in 1995 found that death rate, length of stay, and medical costs were twice as high for *S. aureus*-associated hospitalizations compared with other hospitalizations. *S. aureus* bacteremia is a prominent cause of morbidity and mortality in hemodialysis patients with an annual incidence of three to four percent. Contributing to the seriousness of *S. aureus* infections is the increasing percentage of isolates resistant to methicillin, and early reports of resistance to vancomycin. Hence, immunoprophylaxis against *S. aureus* is highly desired.

The capsular polysaccharides (CPS) of *S. aureus* are virulence factors in systemic infections caused by this opportunistic pathogen. *S. aureus* CPS confer invasiveness by inhibiting opsonophagocytic killing by polymorphonuclear neutrophils (PMN), similar to other encapsulated bacteria, such as *Streptococcus pneumoniae*. This enables the bacteria to persist in the blood, where they elaborate several different virulence factors, including toxins and extracellular enzymes. Of the 13 known types of *S. aureus*, Types 5 and 8 account for approximately 85 percent of all clinical isolates. Nearly all of the remaining isolates are of Type 336 that carries a more recently identified polysaccharide (PS) antigen known as 336PS. Antibodies to Types 5 and 8 capsular polysaccharides ("T5CPS" and "T8CPS") and 336PS induce type-specific opsonophagocytic killing by human PMNs in vitro, and confer protection against the homologous strain in animal infection models.

*S. aureus* causes several diseases by various pathogenic mechanisms. The most frequent and serious of these diseases are bacteremia and its complications in hospitalized patients. In particular, *S. aureus* can cause wound infections and infections associated with catheters and prosthetic devices. Serious infections associated with *S. aureus* bacteremia include osteomyelitis, invasive endocarditis and septicemia. Staphylococci have developed very sophisticated mechanisms for inducing diseases in humans, including both intracellular and extracellular factors. For instance, *S. aureus* possesses several surface antigens that facilitate its survival in the blood stream by helping the bacteria to evade phagocytic killing by the host leukocytes. These surface antigens include cell wall components such as teichoic acid, protein A, and capsular polysaccharides (CPS). Due in part to the versatility of these bacteria and their ability to produce extracellular products that enhance virulence and pathogenicity, staphylococcal bacteremia and its complications continue to be serious and frequently observed nosocomial infections.

Antibiotics such as penicillin have been used successfully against both staphylococcal and enterococcal infections in humans, but more recently the effectiveness of such antibiotics has been thwarted by the ability of bacteria to develop resistance. For example, shortly after the introduction of methicillin, the first semisynthetic penicillin, strains of methicillin-resistant *S. aureus* (MRSA) were isolated. Antibiotic resistance among staphylococcal isolates from nosocomial infections continues to increase in frequency, and resistant *S. aureus* strains continue to cause epidemics in hospitals in spite of developed preventive procedures and extensive research into bacterial epidemiology and antibiotic development. Enterococci resistant to vancomycin started to appear in 1988 and have now become commonplace among hospital-acquired infections. Although methicillin-resistant *S. aureus* organisms with intermediate resistance to vancomycin have been identified in some centers, it was only recently that three *S. aureus* strains with complete resistance to vancomycin were reported. This suggests that the probable conjugal transfer of vancomycin resistance from Enterococci to Staphylococci has become a reality, and dissemination of these strains could eventually lead to the widespread development of organisms that are more difficult to eradicate. The problem is compounded by multiple antibiotic resistance in hospital strains, which severely limits the choice of therapy.

The initial efficacy of antibiotics in treating and curing staphylococcal infections drew attention away from immunological approaches for dealing with these infections. Although multiple antibiotic-resistant strains of *S. aureus* have emerged, other strategies such as vaccines have not been developed. In addition, passive immunization has been tested for use in immune-compromised individuals, such as neonates, who are at increased risk for contracting these bacterial infections. The data failed to support a solid conclusion in recommending the use of passive immunization in this population. Baker et al., *New Engl. J. Med.* 35:213-219 (1992); Fanaroff et al., *New Engl. J. Med.* 330:1107-1113 (1994).

While polysaccharide vaccines have been developed for some primary bacterial pathogens that induce acute diseases in normal individuals, namely, *Streptococcus pneumoniae, Neisseria meningitidis* and *Hemophilus influenzae*, prior to development of StaphVAX® (Nabi Biopharmaceuticals, Rockville, Md.), none had been described specifically for protection against opportunistic bacteria.

StaphVAX® is a conjugate vaccine against two serotypes of *S. aureus*: Type 5 and Type 8. In the 1980s, eight different serotypes of *S. aureus* were identified using polyclonal and monoclonal antibodies to capsular polysaccharide (CPS). Karakawa et al., *J. Clin. Microbiol.* 22:445 (1985). (The contents of this document and all others listed herein are incorporated herein by reference in their entirety.) Surveys have shown that approximately 85% of isolates are capsular polysaccharide Type 5 or Type 8. More recently, Nabi Biopharmaceuticals has identified and patented an antigen, 336PS, which is found on newly discovered serotype Type 336 of Staphylococcus aureus. This serotype accounts for approximately 10-12 percent of all clinically significant S. aureus infections. In the present context, a "clinically-significant" bacterial strain is one that is pathogenic in humans. The antigen was identified, purified and characterized, and a prototype conjugate vaccine based on the antigen demonstrated the ability to protect animals from challenge with clinical isolates of the homologous serotype. Nabi Biopharmaceuticals is developing a second generation of StaphVAX® vaccine that will contain 336PS antigen in addition to S. aureus Types 5 and 8 antigens. These second-generation vaccines are expected to provide coverage for nearly 100% of all clinically significant S. aureus infections.

In addition to S. aureus, Staphylococcus epidermidis is another clinically significant Gram-positive bacterium that causes hospital-acquired infections. S. epidermidis PS1 Conjugate Vaccine is an investigational vaccine in clinical development for the prevention of S. epidermidis infections. This vaccine has been shown to induce antibodies that are protective in animal models and facilitate elimination of bacteria by the same type of immune system response as StaphVAX®.

Nabi's investigational S. epidermidis vaccine provides a solution for the problem of antibiotic resistance in S. epidermidis. However, there was no reason to expect that a vaccine based on this investigational vaccine would be effective in protecting individuals against infection by non-homologous strains of bacteria.

SUMMARY OF THE INVENTION

The present inventors have found that conjugates of an antigen isolated from one type of S. epidermidis are effective in protecting against bacterial infection by strains of bacteria other than those that are classified as the same type when serotyped. More particularly, a conjugate vaccine comprising the S. epidermidis antigen confers protection against infection by other S. epidermidis strains, other coagulase-negative Staphylococcus and against S. aureus. In particular, it confers protection against infection by both the Type 336 of S. aureus that is described in U.S. Pat. No. 5,770,208, and the mixed Type 336/5 and Type 336/8 strains of S. aureus that are described in co-pending application Ser. No. 11/101,386. It also provides protection against infection by other strains of S. epidermidis that are not of the same serotype as the strain from which the antigen is isolated. This was entirely unexpected as it was not known that conjugates of this S. epidermidis antigen could stimulate the production of antibodies that combat bacterial infection by strains other than the homologous strain. Absent such a teaching, the scope of protection offered by conjugate vaccines of the S. epidermidis antigen could not have been expected.

Type 336/5 and 336/8 are strains that type as Type 5 and Type 8 S. aureus, but which are serologically cross-reactive with antibodies that are raised against 336PS conjugate (336PS covalently bound to protein) vaccine. These strains therefore type serologically as both Type 336 and one of Type 5 or Type 8. They are denoted herein as "mixed Type 336/5" and "mixed Type 336/8," and account for approximately 29% of clinically significant isolates. Serotyping of S. aureus clinical isolates from bacteremic patients showed that the 336 phenotype was present on 37% of all the clinical isolates, with 8% 336, 13% 336/5, and 16% 336/8.

Based on the inventors' discovery, a method now is provided for preventing infection in a population of patients at risk for infection by various species of Staphylococcus comprising administering to a patient in the population a composition comprising a conjugate of an isolated S. epidermidis antigen that contains an N-acetyl-glucosamine linked to glycerol phosphate, wherein the antigen binds with antibodies to S. epidermidis deposited under ATCC 55254. The antigen is denoted herein as PS1. Upon administration to humans as well as animals the conjugate of the isolated S. epidermidis antigen induces production of antibodies that protect against the homologous serotype and species or serotype of Staphylococcus other than S. epidermidis homologous to ATCC 55254. The present invention further provides a method for preventing infection in a population of patients at risk for infection by coagulase-negative Staphylococcus and coagulase-positive Staphylococcus aureus, comprising administering to a patient in the population a composition comprising a conjugate of an isolated S. epidermidis antigen that contains an N-acetylglucosamine linked to glycerol phosphate, wherein the antigen binds with antibodies to S. epidermidis deposited under ATCC 55254. Conjugates of the isolated S. epidermidis antigen produce antibodies that protect against S. aureus. The antigen comprises a 1,3-poly(glycerol phosphate) polymer chain and N-acetyl-glucosamine residues attached to the 2-position of the glycerol.

Also provided is a method for preventing and treating infection in a population of patients at risk for developing infection by various species of Staphylococcus or various types of Staphylococcus epidermidis, comprising administering to a patient in the population a composition comprising antibodies to a conjugate containing an isolated S. epidermidis antigen that contains an N-acetyl-glucosamine linked to glycerol phosphate, wherein the antigen binds with antibodies to S. epidermidis deposited under ATCC 55254. The conjugate of the isolated S. epidermidis antigen produces antibodies that protect against various species of Staphylococcus other than strains homologous to S. epidermidis deposited under ATCC 55254. The present invention also provides a method for preventing and treating infection in a patient diagnosed as having a Staphylococcus infection, comprising administering to the patient a composition comprising antibodies to an isolated S. epidermidis antigen that contains an N-acetyl-glucosamine linked to glycerol phosphate, wherein the antigen binds with antibodies to S. epidermidis deposited under ATCC 55254.

DETAILED DESCRIPTION OF SPECIFIC EMBODIMENTS

Figure 1:
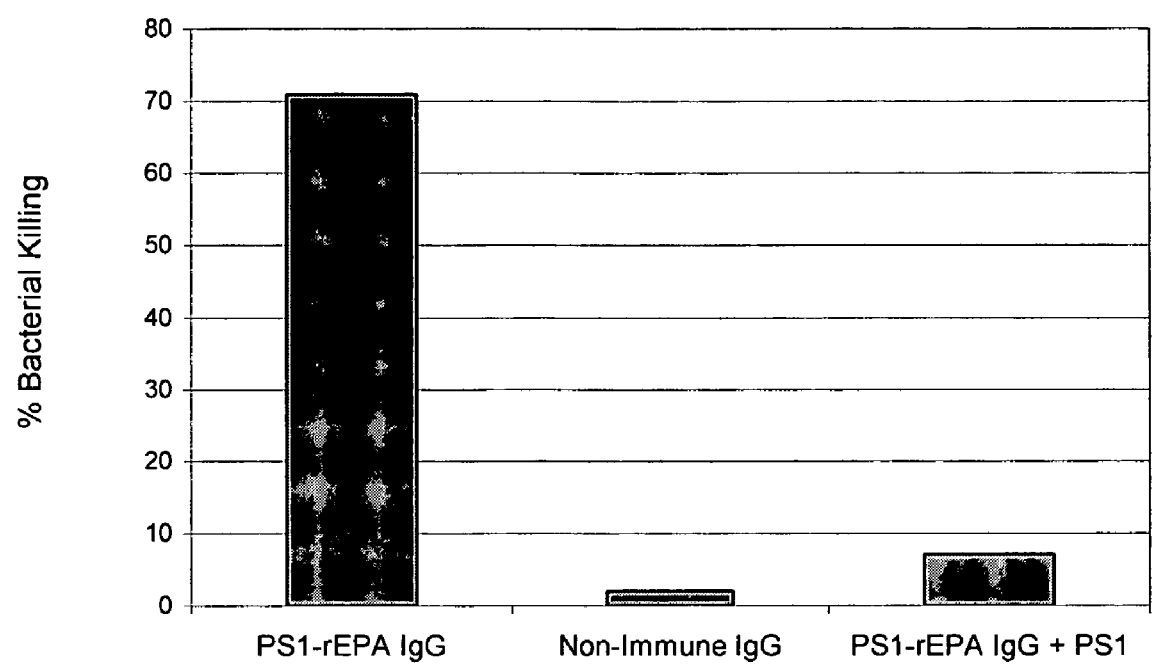
FIG. 1 shows PS1-rEPA rabbit antibody mediated opsonophagocytic Killing of S. epidermidis 956 and effective removal of opsonic Antibody Activity by PS1 Antigen.

It surprisingly has been discovered that vaccines based on conjugates of PS1 can effectively protect individuals against bacterial infection not only by homologous strains of bacteria that type as S. epidermidis strains, but also by strains of S. epidermidis that are not homologous to S. epidermidis deposited under ATCC 55254, as well as by strains of S. aureus. There are very few polysaccharide-based vaccines that provide protection against bacterial infection, and protection against non-homologous strains of bacteria has not been reported for any of these. Accordingly, it was quite surprising to discover that a conjugate vaccine based on antigen isolated from a strain homologous to ATCC 55254 of S. epidermidis provided protection against some non-homologous strains of S. epidermidis and against strains of S. aureus.

Quite unexpectedly, antibodies generated in response to a PS1 conjugate vaccine also possess the ability to protect against infections in which S. aureus is the causative organism. IgG derived from PS1 conjugate vaccine shows cross-reactivity with a S. aureus polysaccharide antigen that is found on clinical isolates. Furthermore, immunoglobulin raised in response to PS1 conjugate vaccine efficiently clears S. aureus bacteremia in a mouse model.

U.S. Pat. Nos. 5,866,140 and 5,961,975 describe a process for extracting antigen from S. epidermidis, and the contents of these documents are incorporated by reference in their entirety. These patents describe that the S. epidermidis antigens provide protection against infection by clinically significant S. epidermidis isolates. In this regard, a "clinically significant" isolate is an isolate that is pathogenic.

The antigen can be obtained in recoverable amounts, from certain S. epidermidis isolates cultured pursuant to the protocols described in further detail herein, in substantially pure form. In particular, purified antigen acceptable for human use contains minimal amounts of other materials such as proteins and nucleic acids, and is of vaccine-grade quality as defined by the FDA. A "recoverable" amount in this regard means that the isolated amount of the antigen is detectable by a methodology less sensitive than radiolabeling, such as immunoassay, and can be subjected to further manipulations involving transfer of the antigen per se into solution.

To obtain PS1, ATCC 55254 or a S. epidermidis isolate homologous thereto can be grown, for example, in Columbia Broth supplemented with 4% NaCl, although other media can be substituted. The preferred medium according to the present invention is a modified Columbia broth (Difco Laboratories, Detroit, Mich.), a medium in which the level of available phosphate is 76 µg/ml. Such a medium simulates the in vivo level of available phosphate in humans, which is about 23-46 µg/ml. Little or no slime is produced when S. epidermidis is grown in this medium.

Following fermentation, cells are killed, and then harvested by centrifugation. Antigen preferably is extracted from cell paste, although PS1 can be extracted from both the cells and the supernatant of clinical isolates of S. epidermidis grown in Columbia broth.

Enzyme treatments of cell paste with lysostaphin, DNase, RNase and optionally protease, followed by sequential precipitation with 25-75% cold ethanol/$CaCl_2$, results in a crude antigen extract. The lyophilized material is dissolved in buffer and loaded onto an ion-exchange column equilibrated with the same buffer. The column is washed with NaCl loading buffer and then eluted with a NaCl gradient. Fractions containing antigen are pooled, dialyzed, and concentrated. Material is then loaded onto a size exclusion column and eluted using a buffer. Fractions containing antigen are pooled, dialyzed, concentrated, and lyophilized. The separation can be repeated to obtain better purification. The foregoing protocol is exemplary; various protocols can be followed to extract and purify PS1 in accordance with the present invention.

Analysis of purified PS1 shows that it comprises N-acetyl-glucosamine and glycerol phosphate. The antigen comprises a 1,3-poly(glycerol phosphate) chain and N-acetyl-glucosamine residues attached to the 2-position of the glycerol. The PS1 antigen thus is chemically distinct from Type 336 antigen, and also is chemically distinct from both the Type 5 and Type 8 S. aureus antigens and from S. aureus teichoic acid.

The reactivities of lipoteichoic acid (LTA) derived from five different G+bacteria other than S. epidermidis (Streptococcus pyogenes, Streptococcus sanguis, Bacillus subtilis, Streptococcus faecalis and S. aureus) PS1, S. aureus 336PS ("336PS") and S. aureus teichoic acid (SA TA) were compared with different monoclonal antibodies and polyclonal antisera using Ouchterlony method. PS1-conjugate antisera and 336PS-conjugate antisera did not precipitate with any of the five LTAs. Although some of these LTAs (S. aureus, S. pyogenes, and S. anguis) reacted with anti-PS1 monoclonal antibody, their reactivity disappeared following treatment of the LTAs with NaOH, whereas NaOH-treated PS1 retained its reactivity. The results clearly demonstrate that lipoteichoic acids are distinctly different compounds from both PS1 and 336PS.

Induction of bacteremia in mammals requires extremely high numbers of organisms or some previous maneuver to lower the host resistance. In vitro phagocytosis mediated by specific antibodies to bacterial polysaccharide, however, can be used as a correlate of protective immunity in vivo. In this model, the ability of PS1-specific monoclonal and polyclonal antibodies to opsonize S. aureus in vitro is measured by phagocytosis, according to the method described in Kojima et al., Infect. Dis. Immun. 58: 2367-2374 (1990). Antibodies induced by a PS1 vaccine facilitate type-specific phagocytosis, and antibodies to PS1 are protective against infection by S. aureus strains that carry 336PS. There was no previous suggestion that antibodies to the conjugate of PS1 would be protective against S. aureus 336 strains.

Bacterial polysaccharides are generally poor immunogens. Polysaccharide antigens normally generate a T-cell independent immune response and they induce humoral antibodies with no boost of the immune response observed upon reinjection. To generate a complete immune response polysaccharides are typically conjugated to T-cell dependent immunogens such as proteins. The direct results of chemical bonding between polysaccharide and protein are to increase the immunogenicity of the polysaccharide and memory response to the antigen potentiating their use in infants and immune-compromised patients. Therefore, for use in a vaccine, it is preferable to conjugate the antigen to an immunocarrier, usually a polypeptide or protein, thereby to improve qualitatively and quantitatively the host humoral immune response specific to the PS1 antigen by recruiting T cells and interaction between T and B cells for the induction of an immune response against the PS1 antigen. This is particularly important for vaccines intended for use in patients with reduced resistance.

An immunocarrier thus enhances immunogenicity both for active immunization, for preparing high-titered antisera in volunteers for passive immunization and for use as an immunogen in the process of making monoclonal antibodies. Suitable immunocarriers according to the present invention include tetanus toxoid, diphtheria toxoid, Pseudomonas aeruginosa Exotoxin A or its derivatives, recombinantly-produced non-toxic mutants of exotoxin A, as described, for example, in Fattom et al., Infect Immun 61: 1023-1032 (1993), as well as other proteins used as immunocarriers.

PS1 can be treated with carabodiimide such as 1-ethyl-3-(3-dimethylaminopropyl)carbodiimide (EDC) and bound, through a linker containing nucleophilic group(s) or without a linker, to a suitable immunocarrier such as a protein, e.g., diphtheria toxoid (DTd), recombinant exoprotein A from Pseudomonas aeruginosa (rEPA), or tetanus toxoid (TTd) or their chemically modified derivatives such as succinylated rEPA. See, for example Kossaczka, et al., *Infect Immun* 65:2088-2093 (1997) The resulting conjugates are separated from unconjugated antigen.

There are other conjugation methods known in the art, e.g., cyanogen bromide (CNBr) (see Schneerson et al., *J. Exp Med* 152:361-376, 1980; Chu et al., *Infect Immun* 40:245-256, 1983) or a-cyano-4-dimethylamino-pyridinium tetrafluoroborate (CDAP) activation of carbohydrates (see Kohn, et al., *FEBS Lett* 154:209-210, 1983 or Kossaczka et al., *Infect Immun* 69:5037-5043, 2000), or periodate oxidation of carbohydrates followed with reductive amination, carbodiimide treatment, and other methods and/or their different combinations that can provide direct or indirect (through a linker) covalent binding of PS1 and carrier protein and thus yield the conjugate. Regardless of the method used to conjugate the antigen to the carrier protein, the covalent binding of PS1 to carrier protein converts PS1 from a T cell independent antigen to a T cell dependent antigen. As a result, PS1-protein conjugate elicits PS1-specific antibody response in immunized animals in contrast to no such response observed upon administering PS1 alone.

Preferably the conjugate is administered without an adjuvant in order to avoid adjuvant-induced toxicity. If an adjuvant is used, it is preferred to use one that promotes humoral immune response and is acceptable for human use, e.g., aluminum hydroxide, aluminum phosphate, QS-21. Efficient adjuvants to be used experimentally include complete Freund's adjuvant (CFA) and incomplete Freund's adjuvant (IFA). A vaccine according the invention additionally may comprise a yeast or a fungal derived β-glucan or its derivatives, in particular, a baker yeast β-glucan as described in U.S. Pat. No. 6,355,625.

The PS1 conjugate according to the present invention is the active ingredient in a composition, which additionally may comprise a pharmaceutically acceptable excipient for the active ingredient. In this regard, a pharmaceutically acceptable excipient is a material that can be used as a vehicle for administering a medicament because the material is inert or otherwise medically acceptable, as well as compatible with the active agent, in the context of vaccine administration. In addition to a suitable excipient, the composition can contain conventional vaccine additives like diluents, adjuvants, antioxidants, preservatives and solubilizing agents. The vaccine can induce production in vivo of antibodies that combat *S. aureus, S. epidermidis* and other coagulase-negative Staphylococcal infections.

Preferably, a composition of the antigen/immunocarrier conjugate according to the present invention "consists essentially of" the conjugate. In this context, the phrase "consists essentially of" means that the composition does not contain any material that negatively impacts the elicitation of an immune response to the antigen (and to other antigens, if present) when the composition is administered to a subject as a vaccine. Preferably the composition does not contain a substantial amount of unconjugated antigen.

The present invention is particularly based on the ability of anti-PS1 antibodies that are elicited in response to PS1 conjugate, to mediate protection against not only homologous strains of bacteria but also against heterologous strains. This results from the heretofore unrealized cross-reactive capacity of antibodies elicited by PS1 conjugate to other surface polysaccharides of other staphylococcal species, strains and serotypes.

The present invention also relates to the use of the PS1 conjugate to produce polyclonal antibodies or monoclonal antibodies (mouse or human) that bind to various Staphylococcal strains that carry PS1 and/or similar antigens that cross-react with antibodies to PS1, thereby mediating their clearance. Protocols for producing these antibodies are described in Ausubel, et al. (eds.), Molecular Cloning: A Laboratory Manual, Cold Spring Harbor Laboratory, Cold Spring Harbor, N.Y.)., Chapter 11; in METHODS OF HYBRIDOMA FORMATION 257-271, Bartal & Hirshaut (eds.), Humana Press, Clifton, N.J. (1988); in Vitetta et al., *Immunol. Rev.* 62:159-83 (1982); and in Raso, *Immunol. Rev.* 62:93-117 (1982).

Inoculum for polyclonal antibody production typically is prepared by dispersing the conjugate in a physiologically-tolerable diluent such as phosphate buffered saline (PBS). An immunostimulatory amount of inoculum, with or without adjuvant, is administered to a mammal and the inoculated mammal is then maintained for a time period sufficient for the antigen to induce protecting PS1 specific antibodies. Boosting doses of the conjugate may be used in individuals that are not already primed to respond to the antigen.

Antibodies can include antibody preparations from a variety of commonly used animals, e.g., goats, primates, donkeys, swine, rabbits, horses, hens, guinea pigs, rats, and mice, and even human antibodies after appropriate selection, fractionation and purification. Animal antisera may also be raised by inoculating the animals with formalin-killed strains of *S. epidermidis* that carry PS1, by conventional methods, bleeding the animals and recovering serum or plasma for further processing.

Hyperimmune PS1-rEPA polyclonal antisera can be raised in rabbits by multiple immunizations with PS1-rEPA conjugate vaccine. Similarly, murine monoclonal antibodies can be developed from primed murine splenocytes, immunized with PS1-rPEA conjugates. Both the rabbit hyperimmune polyclonal antisera and the monoclonal antibodies (ascites and concentrated supernatants) are purified by protein G affinity column chromatography and quantitated either by UV absorbance or BCA methodologies.

The antibodies induced in this fashion can be harvested and isolated to the extent desired by well known techniques, such as by alcohol fractionation and column chromatography, or by immunoaffinity chromatography; that is, by binding antigen to a chromatographic column, passing the antiserum through the column, thereby retaining specific antibodies and separating out other immunoglobulins (IgGs) and contaminants, and then recovering purified antibodies by elution with a chaotropic agent, optionally followed by further purification, for example, by passage through a column of bound blood group antigens or other non-pathogen species. This procedure may be preferred when isolating the desired antibodies from the sera or plasma of humans that have developed an antibody titer against the pathogen in question, thus assuring the retention of antibodies that are capable of binding to the antigen. They can then be used in preparations for passive immunization against strains homologous to ATCC 55254 as well as against heterologous strains of *S. epidermidis*, and even against other species of *Staphylococcus*, in particular against *S. aureus* Type 336.

A monoclonal PS1 specific antibody composition contains, within detectable limits, only one antibody specificity capable of binding to an epitope on PS1 or an epitope of a cross-reactive antigen. Suitable antibodies in monoclonal form can be prepared using conventional hybridoma technology.

To form hybridomas from which a monoclonal antibody composition of the present invention is produced, a myeloma or other self-perpetuating cell line is fused with lymphocytes obtained from peripheral blood, lymph nodes or the spleen of a mammal hyperimmunized with PS1 conjugate. It is preferred that the myeloma cell line be from the same species as the lymphocytes. Splenocytes are typically fused with myeloma cells using polyethylene glycol 1500. Fused hybrids are selected by their sensitivity to hypoxanthine-aminopterin-thymidine (HAT). Hybridomas secreting the antibody molecules of this invention can be identified using an ELISA.

A BALB/c mouse spleen, human peripheral blood, lymph nodes or splenocytes are the preferred materials for use in preparing murine or human hybridomas. Suitable mouse myelomas for use in the present invention include the HAT cell lines, a preferred myeloma being P3X63-Ag8.653. The preferred fusion partner for human monoclonal antibody production is SHM-D33, a heteromyeloma available from ATCC, Manassas, Va. under the designation CRL 1668.

A monoclonal antibody composition of the present invention can be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules then can be isolated further by well known techniques.

Media useful for the preparation of these compositions are both well known in the art and commercially available, and include synthetic culture media, inbred mice and the like. An exemplary synthetic medium is Dulbecco's Minimal essential medium supplemented with 20% fetal calf serum. An exemplary inbred mouse strain is the BALB/c.

Other methods of preparing monoclonal antibody compositions are also contemplated, such as interspecies fusions, since it is primarily the antigen specificity of the antibodies that affects their utility in the present invention. Human lymphocytes obtained from infected individuals can be fused with a human myeloma cell line to produce hybridomas that can be screened for the production of antibodies that recognize PS1. More preferable in this regard, however, is a process that does not entail the use of a biological sample from an infected human subject. For example, a subject immunized with a vaccine as described herein can serve as a source for antibodies suitably used in an antibody composition within the present invention.

In a particularly preferred embodiment, monoclonal antibodies are produced to PS1 using methods similar to those described for type-specific antibodies to S. aureus Type 5, Type 8 and Type 336. The purified monoclonal antibodies are characterized by bacterial agglutination assays using a collection of clinical isolates.

The monoclonal and polyclonal antibody compositions produced according to the present description can be used in passive immunization to introduce antibodies that mediate opsonophagocytosis for the treatment of infection by strains of Staphylococcus that carry PS1 and/or an antigen that cross-reacts with antibodies raised to PS1 conjugate. Such strains include, but are not necessarily limited to, Type 336, Type 336/5, and Type 336/8 S. aureus. In this regard, the antibody preparation can be a polyclonal composition. Such a polyclonal composition may include, in addition to the antibodies that bind to PS1 and/or antigens that cross-react with antibodies raised to the PS1 conjugate, antibodies that bind to the antigens that characterize Type 5 and Type 8 strains of S. aureus. Such a composition can be obtained by immunizing a population with a multivalent vaccine or by mixing antibodies raised in separate populations in response to monovalent vaccines. Thus, the polyclonal antibody component can be a polyclonal antiserum, preferably affinity purified, from an animal that has been immunized with the PS1 conjugate, and preferably also immunized with Type 5 and Type 8 antigen conjugates and GP1 antigen conjugates described in U.S. Pat. No. 6,936,258 Alternatively, an "engineered oligoclonal" mixture may be used, such as a mixture of monoclonal antibodies to PS1, and monoclonal antibodies to the Type 5 and/or Type 8 antigens, and monoclonal antibodies to GP1.

In both types of mixtures, it can be advantageous to link antibodies together chemically to form a single polyspecific molecule capable of binding to PS1 or to a cross-reactive antigen, and to one or both of Type 5 and Type 8 antigens. One way of effecting such a linkage is to make bivalent $F(ab')_2$ hybrid fragments by mixing two different $F(ab')_2$ fragments produced, e.g., by pepsin digestion of two different antibodies, reductive cleavage to form a mixture of Fab' fragments, followed by oxidative reformation of the disulfide linkages to produce a mixture of $F(ab')_2$ fragments including hybrid fragments containing a Fab' portion specific to each of the original antigens. Methods of preparing such hybrid antibody fragments are disclosed in Feteanu, Labeled Antibodies In Biology And Medicine 321-23, McGraw-Hill Int'l Book Co. (1978); Nisonoff, et al., Arch Biochem. Biophys. 93: 470 (1961); and Hammerling, et al., J. Exp. Med. 128: 1461 (1968); and in U.S. Pat. No. 4,331,647.

Other methods are known in the art to make bivalent fragments that are entirely heterospecific, e.g., use of bifunctional linkers to join cleaved fragments. Recombinant molecules are known that incorporate the light and heavy chains of an antibody, e.g., according to the method of Boss et al., U.S. Pat. No. 4,816,397. Analogous methods of producing recombinant or synthetic binding molecules having the characteristics of antibodies are included in the present invention. More than two different monospecific antibodies or antibody fragments can be linked using various linkers known in the art.

An antibody component produced in accordance with the present invention can include whole antibodies, antibody fragments, or subfragments. Antibodies can be whole immunoglobulin of any class, e.g., IgG, IgM, IgA, IgD, IgE, chimeric antibodies or hybrid antibodies with dual or multiple antigen or epitope specificities, or fragments, e.g., $F(ab')_2$, Fab', Fab and the like, including hybrid fragments, and additionally includes any immunoglobulin or any natural, synthetic or genetically engineered protein that acts like an antibody by binding to a specific antigen to form a complex. In particular, Fab molecules can be expressed and assembled in a genetically transformed host like E. coli. A lambda vector system is available thus to express a population of Fab's with a potential diversity equal to or exceeding that of subject generating the predecessor antibody. See Huse, W. D. et al., Science 246: 1275-81 (1989).

The present invention comprehends protecting a human at risk for infection by various species of Staphylococcus including various types of Staphylococcus epidermidis, other coagulase-negative Staphylococci and Staphylococcus aureus The method comprises administering to a patient in such a population a composition comprising a conjugate of PS1. The PS1 conjugate induces the production of antibodies that also protect against a species or type of Staphylococcus other than strains that are homologous to S. epidermidis ATCC 55254. The vaccine is administered in a dose that produces a serotype-specific antibody level in the individual that is sufficient to provide immunity against challenge.

The method can be used to protect against bacterial infection in immune-compromised individuals, and produces in immune-compromised individuals a level of serotype-specific antibody to the antigens contained in the vaccines that is the same, within the limits of expected experimental variation, to the level that is achieved in normal healthy subjects when they are immunized. This was entirely unexpected in light of conventional theory to the effect that immune-compromised individuals cannot be expected to mount an effective immune response against poorly immunogenic antigens such as polysaccharide antigens, which are known for their generally low immunogenicity. There are a large number of immune-compromised populations that benefit from the administration of vaccines according to the present invention. Immune-compromised individuals include end stage renal disease (ESRD) patients; cancer patients on immunosuppressive therapy, AIDS patients, diabetic patients, the elderly in extended care facilities, patients with autoimmune disease on immunosuppressive therapy, transplant patients, and burn patients.

Preferably the PS1-conjugate vaccine or adjuvanted vaccine is formulated to contain a target dose of at least about 5 µg of conjugate and up to about 500 µg of conjugate. Preferably at least 25 µg of conjugate, and more preferably 50, 75, 100 or 200 µg of conjugate is used. A higher initial dose and/or a second dose of the vaccine given after the first dose may be used, particularly in immune-compromised populations because of the anticipated weaker immune response in this chronically-ill population. The vaccine provides a level that is at least two fold greater, and preferably four fold greater, than the prevaccination level.

The vaccine can be used for active protection in immune-compromised individuals that are about to be subjected to conditions that place them at immediate risk of developing a bacterial infection. These conditions would include, for example, catheterization or a surgical procedure. Notably, even immune-compromised individuals may mount an effective immune response when vaccinated with a vaccine according to the present invention.

Pursuant to the present invention, such a vaccine can be administered to a subject not already infected with *Staphylococcus*, thereby to induce a staphylococcal-protective immune response in that subject. Alternatively, a vaccine within the present invention can be administered to a subject in whom staphylococcal infection already has occurred but is at a sufficiently early stage that the immune response produced to the vaccine effectively inhibits further spread of infection. Notably, the PS1 conjugate vaccine can prevent bacteremia from developing.

By another approach, a vaccine of the present invention can be administered to a subject who then acts as a source for globulin, produced in response to PS1 conjugate vaccine ("hyperimmune globulin"), which contains antibodies directed against *Staphylococcus*. subject thus treated would donate plasma from which hyperimmune globulin would then be obtained, via conventional plasma-fractionation methodology, and administered to another subject in order to impart resistance against or to treat staphylococcal infection. Hyperimmune globulins according to the invention are particularly useful for immune-compromised individuals, for individuals undergoing invasive procedures or where time does not permit the individual to produce his own antibodies in response to vaccination.

Similarly, monoclonal or polyclonal antibodies to PS1 of *S. epidermidis* produced according to the present invention can be conjugated to an immunotoxin, and administered to a subject in whom staphylococcal infection has already occurred but has not become widely spread. To this end, antibody material produced pursuant to the present description would be administered in a pharmaceutically acceptable carrier, as defined herein.

The present invention is further described by reference to the following, illustrative examples.

Example 1

Fermentation of *S. epidermidis*

ATCC 55254 was inoculated to Columbia broth (Difco) supplemented with 4% NaCl and grown overnight at 37° C. while shaking. Cells from this starter culture were inoculated into a 50-liter fermentor containing the same medium and fermented at 37° C. with agitation at 200 rpm for 24 hours. For purification of the PS1 antigen, cells were killed by adding phenol-ethanol (1:1, vol/vol, final concentration of 2%) and mixing slowly. The cells were then harvested by centrifugation and the supernatants and cells were pooled.

Example 2

Extraction and Purification of Antigen

The cells were disintegrated with enzymes, lysostaphin or lysozyme, or were extracted with 5% trichloroacetic acid at 4° C. The cells were then centrifuged and the supernatant was precipitated with 25% ethyl alcohol supplemented with 5-10 mM $CaCl_2$. After centrifugation, the supernatant was precipitated with 75% ethyl alcohol supplemented with 5-10 mM $CaCl_2$. The precipitate was pelleted by centrifugation, redissolved in distilled water, dialyzed against distilled water overnight and then lyophilized.

The crude lyophilized extracts were dissolved in sodium acetate buffer at pH 6.0 and were loaded on a DEAE sepharose column equilibrated in the same buffer. After washing the column, the column was eluted with a NaCl gradient in sodium acetate buffer at pH 6.0. Immunoprecipitation using type-specific antisera was used to identify fractions containing antigen.

The fractions containing antigen were pooled, concentrated on an ultrafiltration Amicon membrane, dialyzed against distilled water four times and lyophilized. This procedure was repeated when better purification of the antigen was desired. The purified polysaccharide was sized on a gel filtration column such as a Sephacryl column. The polysaccharide fractions were pooled, concentrated on an ultrafiltration Amicon membrane, dialyzed against distilled water and lyophilized. The result of this purification is PS1 antigen in substantially pure form.

Protein and nucleic acid analysis of the purified PS1 antigen revealed that it contains neither protein nor nucleic acids.

Example 3

Characterization of Antigen

Chemical and Physicochemical Analysis of Purified Antigen.

Complete hydrolysis of the purified PS1 antigen and analysis of the hydrolyzate by HPAEC showed that the major components of the antigen are glycerol and N-acetyl-glucosamine. A phosphorous assay also confirmed the presence of a phosphodiester linkage.

Structural Analysis of Purified Polysaccharide.

Nuclear magnetic resonance analysis of the purified antigen indicated that it is of the teichoic acid type, i.e., a 1,3-poly(glycerol phosphate) chain with N-acetyl-glucosamine attached to the 2-position in a predominantly beta-linkage.

Immunochemical Analysis of *S. epidermidis* PS1.

Purified PS1 reacted with a single precipitin band with whole cell antisera to the prototype *S. epidermidis* strain in a double immunodiffusion assay. The PS1 structure is unique or distinct from that of other known 1,3-poly(glycerol phosphate) teichoic acids and lipoteichoic acids containing N-acetyl-glucosamine, and data demonstrates the non-reactivity of polyclonal PS1 conjugate antiserum with such antigens.

Example 4

Preparation of Antigen-Immunocarrier Conjugates

To make the polysaccharide immunogenic, *S. epidermidis* PS1 was conjugated to a recombinantly-produced, non-toxic *Pseudomonas aeruginosa* exotoxin A (rEPA), or to a succinylated derivative of rEPA, denoted rEPAsuc via 1-ethyl-3-(3-dimethylaminopropyl)-carbodiimide hydrochloride (EDAC). PS1 activated with EDAC was covalently bound to either rEPA or rEPAsuc using adipic acid dihydrazide as the linker ($PS1_{AH}$). Conjugation technology for $PS1_{AH}$-rEPA and $PS1_{AH}$-rEPAsuc is the same except for the different form of protein carrier used in the conjugation, i.e., the unmodified rEPA and succinylated rEPA, rEPAsuc, respectively. In $PS1_{AH}$-rEPA only the carboxyls intrinsic to rEPA can be engaged for linkage. In $PS1_{AH}$-rEPAsuc, the carboxyls of exogenous succinate are utilized in addition to those carboxyls intrinsic to rEPA. Introduction of more carboxyls on the protein leads to a greater incorporation of PS1 into the conjugate and greater yield of conjugate. The conjugate can also be accomplished using other bifunctional linker molecules and/or other carrier proteins.

Replacement of the chemically unmodified recombinant *P. aeruginosa* exoprotein A (rEPA) as the protein carrier with a succinylated rEPA (rEPAsuc) provides higher efficiency of the conjugation reaction and consequently a significant increase in yield of the conjugate. Both conjugate types retain reactivity with PS1-specific antibodies as well as antibodies specific to *P. aeruginosa* Exotoxin A. Immunogenicity testing of conjugates indicated that the conjugates with rEPAsuc, denoted as $PS1_{AH}$-rEPAsuc, elicited equally high titers of serum IgG specific to PS1 (α-PS1 IgG) as those containing the unmodified rEPA, denoted $PS1_{AH}$-rEPA.

Example 5

Immunogenicity of *S. epidermidis* PS1 Conjugate Vaccine

It is commonly appreciated that bacterial polysaccharides are T-cell independent antigens and as such when administered alone, they do not elicit significant levels of antibodies in naïve populations and small children, i.e., do not trigger an anamnestic immune response. Similar to the vast majority of bacterial polysaccharides, *S. epidermidis* PS1 antigen alone (unconjugated to protein) did not elicit a specific antibody immune response.

To evaluate immunogenicity, $PS1_{AH}$-rEPA, purified PS1, and purified PS1 and rEPA non-covalently bound were administered subcutaneously (SQ) 3 times at 100 μL/injection, 2 weeks apart into groups of ten outbred mice (ICR). Seven days following the third injection, mice were exsanguinated and sera were collected. Most of the conjugates were tested at 2.5 μg and 5 μg doses; the injection dose of the conjugate was based on PS1 content. Some conjugates were tested over a broader dosage range of 0.25, 2.5, 5, and 10 μg/injection.

Immunogenicity was evaluated based on the titer of serum IgG specific to PS1 (α-PS1 [IgG]) measured by ELISA using PS1 as the coating antigen. ELISA plates were coated with PS1 polysaccharide at optimum coating concentration overnight at room temperature. Plates were washed and blocked with BSA to prevent the non-specific binding of antibodies. Serial dilutions of sera were made and the mouse antibodies bound to PS1 were detected by an enzyme-linked anti-mouse IgG secondary antibody. Immunogenicity results are presented as the group geometric mean (GM) values of serum α-PS1 [IgG] expressed in ELISA units/mL. Titers of serum samples were compared to the reference serum with a known concentration of PS1-specific antibodies.

As expected, PS1 did not induce a specific antibody response in mice even upon being administered 3 times 2 weeks apart. In order to change PS1 from a T-cell independent to a T-cell dependent antigen that would elicit a PS1 specific antibody response in the host, PS1 was conjugated to rEPA as described above. Following conjugation to the rEPA, PS1 became immunogenic and induced significant antibody levels (see Table 1).

TABLE 1

Comparison of PS1-Specific Antibody Responses to PS1-rEPA Conjugate and PS1 Alone or as a Mixture with rEPA

| Type of Conjugate | Geometric Mean Anti-PS1 IgG (ug/mL) |
|---|---|
| $PS1_{AH}$-rEPA | 150 |
| PS1 | 0.6 |
| PS1 + rEPA | 0.1 |
| PBS Buffer | 0.3 |

Immunogenicity of the two types of conjugates ($PS1_{AH}$-rEPA and $PS1_{AH}$-rEPAsuc) was compared in several studies and the results are summarized in Table 2. Immunogenicity of the conjugates was evaluated based on the titer of serum IgG specific to PS1 (α-PS1 [IgG]) measured by ELISA using PS1 as the coating antigen as described above. Immunogenicity results are presented as the group geometric mean (GM) values of serum α-PS1 [IgG] expressed in ELISA units/mL. Titers of serum samples were compared to the reference serum arbitrarily assigned 100 U/mL. The titer of 100 ELISA Units/mL represents the concentration of specific IgG that gives $OD_{450}$ of 2.0 at the dilution of 1:2000 in ELISA.

All conjugates were highly immunogenic following 3 injections. GM values of IgG specific to PS1 were in the range of 100 to 300 U/mL and there were no non-responders to PS1-conjugates (Table 2). In terms of immunogenicity, there was no significant difference between lots of $PS1_{AH}$-rEPA and $PS1_{AH}$-rEPAsuc; therefore, succinylation of rEPA did not affect the capacity of rEPA as a carrier protein. There was also no significant difference among immunogenicity results obtained with conjugates prepared from different PS1 lots.

TABLE 2

Immunogenicity of the PS1-Conjugates Measured 7 days Following Third Injection of Conjugate Administered at 2.5 μg/dose in 3 Dose Regimen

| Type of Conjugate | Conjugate ID | Geometric mean anti-PS1 IgG (ELISA units/mL) |
|---|---|---|
| $PS1_{AH}$-rEPA | $PS1_{AH}$-rEPA | 285 |
|  | $PS1_{AH}$-rEPA | 171 |

TABLE 2-continued

Immunogenicity of the PS1-Conjugates Measured 7 days Following Third Injection of Conjugate Administered at 2.5 µg/dose in 3 Dose Regimen

| Type of Conjugate | Conjugate ID | Geometric mean anti-PS1 IgG (ELISA units/mL) |
|---|---|---|
| PS1$_{AH}$-rEPASUC | PS1$_{AH}$-rEPA | 152 |
| | PS1$_{AH}$-rEPA | 116 |
| | PS1$_{AH}$-rEPASUC | 198 |
| | PS1$_{AH}$-rEPASUC | 275 |
| | PS1$_{AH}$-rEPASUC | 194 |
| | PS1$_{AH}$-rEPASUC | 159 |
| | PS1$_{AH}$-rEPASUC | 174 |
| | PS1$_{AH}$-rEPASUC | 161 |

Based on the results from conjugate-dosing studies, the optimum dose seemed to be 2.5 µg conjugate/injection. Although some conjugates elicited the same titer levels at 0.25 µg and 2.5 µg doses, for most the latter dose elicited higher titers. At doses greater than 2.5 µg/injection, immune response to the conjugates seemed to decline. There was no obvious dose dependent effect on immunogenicity of either PS1$_{AH}$-rEPA or PS1$_{AH}$-rEPAsuc conjugates following 3 injections at the dose range of 0.25-5 µg. However, due to consistently more uniform and higher immune responses at the 2.5 µg than at the 0.25 µg dose, the former seems to be the optimum dose.

Example 6

In Vitro Opsonophagocytic Activity of *S. Epidermidis* PS1 Conjugate Vaccine Against *S. Epidermidis* and *S. Aureus*

The capability of PS1-rEPA derived rabbit antibodies to mediate opsonophagocytic killing of *S. epidermidis* strain expressing PS1 polysaccharide was evaluated using ATCC 55254. The procedure for conducting the opsonophagocytic assay is described below.

ATCC 55254 was first cultured overnight at 37° C. for single colonies on trypticase soy agar (TSA) plates. From this culture, a single bacterial colony was selected and inoculated to 15 mL of Columbia broth supplemented with 4% sodium chloride and grown overnight at 37° C. while shaking at 200 rpm. The following day, 10 mL of the bacterial culture was centrifuged at 300 rpm for 10 minutes. The resulting pellet was suspended in 10 mL of saline and adjusted to an OD$_{650}$ of 0.1. This solution was diluted 20 times in minimum essential media (plain-MEM) and used as bacterial stock solution. The neutrophil source for the assay was dimethyl sulfoxide (DMSO) induced human HL-60 cells. Prior to performing the assay, cells were centrifuged for 5 minutes at 1000 rpm and the pellet was adjusted to 1×10$^7$ cells/mL in opsonization media (minimum essential medium supplemented with 0.1% gelatin). Eighty fold diluted human plasma from healthy donors was used as complement. The *S. epidermidis* opsonophagocytic assay was conducted by adding 50 µL bacteria, 50 µL complement, 50 µL of HL-60 cells and 50 µL of diluted PS1-rEPA derived rabbit antibodies to the wells of a polystyrene round bottom micro-titer plate. Sample aliquots were taken at the start of the assay (Time 0), and after incubation (Time 60 minutes) at 37° C., plated on trypticase soy agar plates and incubated overnight at 37° C. for bacterial enumeration. The percent opsonic killing was calculated as follows:

$$\% \text{Killing} = \frac{\text{(Time 60 minutes bacterial counts)} \times \text{(Dilution)}}{\text{(Time 0 bacterial counts)} \times \text{(Dilution)}} \times 100$$

The results showed *S. epidermidis* bacterial killing in the presence of PS1 specific rabbit antibodies, but not in the presence of non-immune antibodies (FIG. 1). The opsonic antibody activity could be absorbed with PS1 polysaccharide, thus clearly demonstrating that this opsonic activity was PS1 antigen specific.

Figure 2:
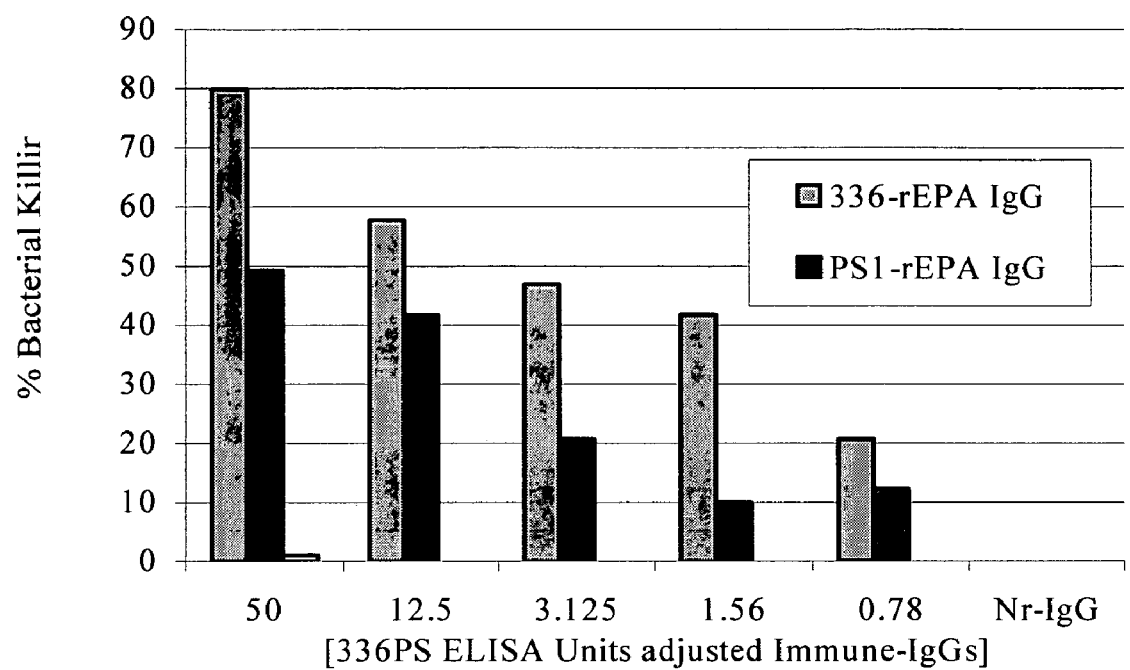
FIG. 2 shows S. aureus 336 opsonophagocytosis by PS1-rEPA immune rabbit sera.

The capability of PS1-rEPA antibodies to mediate cross-opsonophagocytic killing of *S. aureus* 336 strain was evaluated using purified polyclonal rabbit 336-rEPA and PS1-rEPA antibodies at equivalent 336PS ELISA Units. The results indicate that PS1-rEPA antibodies are effective in mediating opsonophagocytic killing of *S. aureus* 336 strain (FIG. 2).

Example 7

Efficacy of PS1 Conjugate-Derived Antibodies in Clearing *S. Epidermidis* Bacteremia The ability of PS1 conjugate to clear staphylococcal bacteremia was assessed. Due to the poor pathogenicity of *S. epidermidis*, a ≧10$^8$ CFU challenge dose is required to cause lethality in mice, while a slight decrease in challenge dose gives a high degree of survival. In order to capitalize on this phenomenon, a sub-lethal challenge of 5×10$^7$ CFU along with five percent hog mucin was used to cause <10% lethalities while surviving mice remained bacteremic for at least 48 hours. As the number of times an individual mouse can be bled is limited, groups of ten challenged mice were randomly sacrificed and bacteremia per individual animal at each data point was evaluated. Using this standardized bacteremia model, antibody-mediated protection against *S. epidermidis* infection was demonstrated, both by passive administration of PS1-rEPA derived antibody and also by active immunization with PS1-rEPA vaccine.

To standardize the *S. epidermidis* bacteremia murine model, three different *S. epidermidis* PS1 serotype clinical infection isolates, ATCC 55254, *S. epidermidis* isolate V01048 (National Institutes of Health/Walter Reed), and *S. epidermidis* isolate CNS10 (University of Virginia, isolated 2002), were tested in the challenge model. Upon receipt at the animal facility, six week old outbred female ICR mice were ear tagged, housed ten mice per cage, and quarantined for a week prior to the study start. The challenge was prepared by growing *S. epidermidis* strains ATCC 55254, V01048 and CNS10 at 37° C. for ~20 hours in 10 mL of Columbia media supplemented with 4% sodium chloride, while shaking at 200 rpm. On the day of challenge, each strain was suspended in saline to an OD$_{540}$ of 0.4 (~4×10$^8$ CFU/mL), diluted to ~2.0× 10$^8$ CFU/mL, mixed at equal volumes with 10% Hog Mucin and ~5.0×10$^7$CFU/500 µL administered intraperitoneally per mouse.

To quantitate bacteremia, five mice per challenge strain were exsanguinated at 6, 24 and 30 and 48 hours post-challenge. For each mouse, a sterile blood culture was obtained via cardiac bleed and 50 µL of blood were plated onto tryptic soy agar plates (TSA) at undiluted, 10-, 100- and 1000-fold dilutions. At the last timepoint (48 hours), a 100 µL blood sample from each mouse was directly plated onto TSA plates. The plates were incubated overnight at 37° C. and the resulting colonies were quantitated.

All three S. epidermidis challenge strains showed equivalent persistence in the blood. At 6 hours post-challenge, all randomly exsanguinated mice showed ≧$10^4$ CFU, irrespective of challenge strain, and bacteria levels remained high through 30 hours post-challenge. By 48 hours after challenge, mice challenged by S. epidermidis ATCC 55254 remained bacteremic with a mean of 5×$10^2$ CFU, while only 3 of 5 mice challenged by S. epidermidis V01048 were bacteremic. For mice challenged by S. epidermidis CNS10, there were 2 lethalities, and 2 of the 3 surviving mice had ≧$10^2$ CFU bacteria. Based on bacteremic persistence and lack of lethalities, the S. epidermidis ATCC 55254 strain was selected as the challenge strain for the S. epidermidis bacteremia model. Table 3 describes the bacteremia per group from this study.

CFU/mL, with 15/17 mice having >$10^2$ CFU/mL. In comparison, in non-immune IgG treated mice, the mean bacteremia was 9.8×$10^5$ CFU/mL, with 14/14 mice having >$10^2$ CFU/mL. The response in saline treated mice was similar to that of non-immune IgG treated mice.

By 30 hours post-challenge, only 65% (11/17) of the mice in the PS1 IgG group were bacteremic, with an average of 3.2×$10^3$ CFU/mL. In the non-immune group, 89% (16/18) of the mice were bacteremic with 6.74×$10^5$ CFU/mL The bacteremia clearance trend in PS1 IgG treated mice remained the same at 48 hours. In the PS1 IgG group, 47% (8/17) of mice were bacteremic with an average of 4.4×$10^2$ CFU/mL, as compared to 65% (11/17) of mice in the non-immune group with mean bacteremia of 6.4×$10^2$ CFU/mL. At

TABLE 3

Timecourse of Bacteremia in Mice Following a S. epidermidis/5% Mucin Saline Challenge

| Challenge Strain | Geometric Mean of CFU/mL in Positive* Sera (range in CFU/mL) Number of bacteremic Mice per Group | | | |
|---|---|---|---|---|
| | 6 Hours | 24 Hours | 30 Hours | 48 Hours |
| S. epidermidis ATCC 55254 | 4.33 × $10^4$ (3 × $10^4$-5.9 × $10^4$) 5/5 | 2.56 × $10^5$ (1.4 × $10^5$-8.8 × $10^5$) 5/5 | 2.52 × $10^5$ (7.1 × $10^4$-9.9 × $10^5$) 5/5 | 5 × $10^2$ (2.8 × $10^2$-1.01 × $10^3$) 5/5 |
| S. epidermidis V01048 | 6.53 × $10^4$ (3.7 × $10^4$-8 × $10^4$) 5/5 | 1.6 × $10^5$ (1.6 × $10^5$-6.99 × $10^5$) 5/5 | 8.77 × $10^4$ (1.0 × $10^4$-1.8 × $10^6$) 5/5 | 5.15 × $10^2$ (4.3 × $10^2$-6.8 × $10^2$) 3/5 |
| S. epidermidis CNS 10 | 8.00 × $10^4$ (5.6 × $10^4$-9.4 × $10^4$) 5/5 | 5.31 × $10^4$ (4 × $10^4$-9.13 × $10^4$) 5/5 | 5.78 × $10^5$ (1.4 × $10^5$-1.8 × $10^6$) 5/5 | 7.8 × $10^2$ (1.1 × $10^3$-1.12 × $10^3$) 2/3 |

*A positive sample had counts ≧$10^2$ CFU/mL.

The efficacy of passively administered PS1-rEPA antibodies in clearing S. epidermidis was tested in the standardized bacteremia model. One day prior to bacterial challenge, mice were administered 3 mg total IgG of either PS1-rEPA rabbit IgG, or non-immune rabbit IgG, or saline. At various times after bacterial challenge animals were sacrificed, serum samples collected, and the number of CFU/mL was determined The results indicated that all challenged mice developed bacteremia (range of $10^5$-$10^6$ CFU/mL) within 6 hours (See Table 4.)

48 hours, 88% (14/16) of mice in the saline group were bacteremic with a mean of 1.6×$10^3$ CFU/mL To demonstrate that PS1-rEPA vaccine induces an effective host antibody response able to clear S. epidermidis infection, 40 female ICR mice were SQ immunized three times, two weeks apart, with 2.5 μg PS1-rEPA vaccine and QS-21 adjuvant. Adjuvant was used to enhance immunogenicity. As a control, another group of mice was given QS-21 alone. On day 35, mouse sera were collected by orbital bleed and specific antibody titers were quantitated by ELISA. Immunoge-

TABLE 4

Effect of PS1-rEPA Rabbit Antibodies in S. epidermidis Bacteremia

| Treatment | Geometric Mean of CFU/mL in Positive* Sera (range in CFU/mL) Number of bacteremic Mice per Group | | | |
|---|---|---|---|---|
| | 6 Hours | 24 Hours | 30 Hours | 48 Hours |
| PS1-rEPA | 4.8 × $10^5$ (1.3 × $10^5$-3.5 × $10^6$) 17/17 | 6.3 × $10^4$ (0-7.7 × $10^5$) 15/17 | 3.2 × $10^3$ (0-4.2 × $10^4$) 11/17 | 4.4 × $10^2$ (0-1.7 × $10^3$) 8/17 |
| Non-Immune IgG | 5.4 × $10^5$ (2.9 × $10^4$-1.7 × $10^6$) 18/18 | 9.8 × $10^5$ (3.2 × $10^5$-3.4 × $10^6$) 14/14 | 6.7 × $10^4$ (5.0 × $10^3$-3.7 × $10^5$) 16/18 | 6.4 × $10^2$ (100-4900) 11/17 |
| Saline | 9.5 × $10^5$ (2.1 × $10^5$-2.9 × $10^6$) 17/17 | 7.2 × $10^5$ (3.0 × $10^5$-1.2 × $10^7$) 17/17 | 1.5 × $10^5$ (8.7 × $10^3$-8.1 × $10^5$) 17/17 | 1.6 × $10^3$ (0-6.4 × $10^3$) 14/16 |

*A positive sample had counts ≧$10^2$ CFU/mL.

Differences in bacteremia clearance among treatment groups became apparent within 24 hours post-challenge. In PS1 IgG treated mice, the mean bacteremia was 6.3×$10^4$ nicity data demonstrated that 100% of mice responded with a peak mean titer after 3 immunizations of 651 EU/mL (range: 151-1920 EU/mL). All mice were challenged on day 36 with S. epidermidis ATCC 55254 (~5.0×10⁷ CFU) in 5% hog mucin by intraperitoneal injection. At various times after bacterial challenge animals were sacrificed, serum samples collected, and the number of CFU/mL was determined At 6 hours post-challenge, all mice developed bacteremia at 1×10⁶ CFU/mL. At 24 hours post-challenge, bacteremia clearance was more rapid in PS1-rEPA/QS-21 treated mice, compared to mice that received QS-21 alone. This was reflected by both the overall decrease in bacteremia as well as in total number of mice that had cleared bacteremia. Results are shown in Table 5.

days and survivors sacrificed by cervical dislocation. The lethal challenge dose was one that caused 100% lethalities within 48 hours of challenge.

All active immunizations were done through subcutaneous immunizations. Mice were immunized three times, 14 days apart with 2.5 μg of vaccine in 10 μg of QS-21 adjuvant. Seven days post last immunization, all mice were orbital bled and sera evaluated for specific antibodies in quantitative ELISA.

BALB/c mice were immunized SQ with either 2.5 μg PS1-rEPA or 336-rEPA+10 μg QS-21 on day 0, 14, 28. On day 35, mice were intraperitoneally primed with phosphate buffered

TABLE 5

Effect of PS1-rEPA Vaccination in Host Ability to Clear S. epidermidis Bacteremia

| Immunogen | Antibody Titer (Range) PS1 IgG (EU/mL) | Geometric Mean in CFU/mL of Positive* Sera (range in CFU/mL) Number of bacteremic Mice per Group | | | |
|---|---|---|---|---|---|
| | | 6 hours | 24 Hours | 30 Hours | 48 Hours |
| PS1-rEPA QS-21 | 651 (151-1920) 40/40 | $1.7 \times 10^5$ $(2.4 \times 10^4\text{-}8.4 \times 10^5)$ 10/10 | $2.2 \times 10^4$ $(2.2 \times 10^3\text{-}7.8 \times 10^5)$ 7/10 | $1.5 \times 10^3$ $(5.2 \times 10^2\text{-}2.16 \times 10^3)$ 4/10 | $2 \times 10^2$ $(10^2\text{-}2.15 \times 10^2)$ 3/10 |
| QS-21 | <0.1 | $2.1 \times 10^5$ $(1.1 \times 10^4\text{-}1.9 \times 10^5)$ 10/10 | $1.1 \times 10^5$ $(2.6 \times 10^3\text{-}4.2 \times 10^6)$ 10/10 | $2.0 \times 10^4$ $(3.7 \times 10^3\text{-}5.1 \times 10^4)$ 8/10 | $8.9 \times 10^2$ $(4 \times 10^2\text{-}2 \times 10^3)$ 9/10 |

*A positive sample had counts ≥10² CFU/mL.

As in the passive immunization study, at 6 hours post-challenge, all mice developed bacteremia of 10⁵ CFU/mL. At 24 hours post-challenge, PS1-rEPA vaccinated mice were clearing bacteremia faster than mice given only the adjuvant. At the 24 hour time point, 70% (7/10) of mice in the PS1-rEPA group had bacteremia >10² CFU (mean bacteremia 2.2×10⁴ CFU/mL). By comparison, the adjuvant-treated group was 100% bacteremic (1.1×10⁵ CFU/mL).

At 30 hours post-challenge, 40% (4/10) of PS1-rEPA vaccinated mice had a bacteremia of 1.5×10³ CFU/mL, as compared to 80% (8/10) of mice in the control group with bacteremia of 2×10⁴ CFU/mL (p=0.08). At 48 hours, 30% (3/10) of PS1-rEPA vaccinated mice were bacteremic, as compared to 90% (9/10) in the control group, with a mean bacteremia of 8.9×10² CFU/mL.

As shown in Example 6, opsonophagocytic antibodies were generated following PS1-rEPA vaccination. In vitro, these opsonic antibodies induced ≥70% opsonic killing of S. epidermidis ATCC 55254 which express the PS1 antigen. This antibody-mediated opsonic killing is absorbed by PS1 polysaccharide. Furthermore, PS1 specific IgG is effective in clearing S. epidermidis induced bacteremia both by passive administration and by vaccination with PS1-rEPA.

Example 8

Cross-Protection Against Type 336 S. Aureus By PS1-rEPA Active Immunization

A lethal challenge model was developed for S. aureus 336. A S. aureus 336 prototype strain was inoculated to 10 mL of Columbia broth supplemented with 4.3% MgCl₂/0.65% CaCl₂ and grown overnight at 37° C. On the day of challenge, bacterial cells were suspended in PBS and then further diluted to ~8×10⁵ CFU/mL, mixed at equal volumes with 10% hog mucin and 500 μL challenge was administered intraperitoneally (ip) per mouse. Mortalities were observed for next five saline and challenged the next day with S. aureus 336 prototype isolate. At the conclusion of the study, mice that had been immunized with 336-rEPA vaccine showed 100% survival rate, as compared to 80% with S. epidermidis PS1-rEPA vaccine and 0% with PBS vaccination (Table 6).

TABLE 6

Cross-Protection Against S. aureus 336 Lethal Challenge by Active Immunization with PS1-rEPA

| Vaccine | Bacterial Challenge | Post-Challenge Survival (Percent Survival) | | |
|---|---|---|---|---|
| (Day 0, 14, 28) | (Day 36) | 24 hr | 40 hr | 5-7 Days |
| PS1-rEPA | ~2.5 × 10⁵ CFU/500 μL of S. aureus 336, 5% Hog Mucin/PBS solution | 8/10 | 8/10 | 8/10 (80%) |
| 336-rEPA | | 10/10 | 10/10 | 10/10 (100%) |
| PBS | | 2/10 | 1/10 | 1/10 (10%) |

Example 9

Cross-Protection Against Type 336 S. Aureus by PS1 Monoclonal Antibodies

Murine monoclonal antibodies which either recognized both PS1 and 336 isolates or PS1 isolates alone were developed from primed murine splenocytes, immunized with PS1-rEPA conjugates. The monoclonal antibodies (ascites and concentrated supernatants) were purified by protein G affinity column chromatography and quantitated either by UV absorbance or BCA methodologies.

Forty-eight hours prior to challenge six-week-old female BALB/c and or ICR mice were immunized SQ with appropriate immunoglobulins. BALB/c mice were immunized SQ with 500 μg of appropriate monoclonal antibody 48 hours prior to challenge. On following day, mice were interperitoneally primed with phosphate buffered saline and challenged the next day with a different S. aureus 336 prototype isolate. There was cross-protection against S. aureus 336 challenge by monoclonal antibodies that had been generated through S. epidermidis PS1-rEPA immunizations (Table 7).

TABLE 7

Cross-Protection Against S. aureus 336 Lethal Challenge by Passive Immunization with S. epidermidis PS1 Monoclonal Antibodies

| S.Q Immunization (500 µg Dose) (Day − 2) | Bacterial Challenge (IP) (Day 0) | Post-Challenge Survival (Percent Survival) | | |
|---|---|---|---|---|
| | | 24 hr | 40 hr | 5-7 Days |
| S. epidermidis PS1-159 (PS1/336 Reactive) | ~2.5 × 10$^5$ CFU/ 500 µL of S. aureus 336, | 37/38 97.4% | 36/38 94.7% | 35/38 92% |
| S. epidermidis PS1-300 (PS1/336 Reactive) | 5% Hog Mucin/ PBS. Serotype: 336 | 14/18 | 13/18 | 13/18 72.2% |
| S. epidermidis PS1-429 (PS1/336 Reactive) | | 12/18 | 11/18 | 11/18 61.1% |
| S. epidermidis PS1-912 (PS1 Exclusive) | | 1/10 | 1/10 | 1/10 10% |
| E. coli 400 | | | 3/28 | 3/28 10.7% |
| PBS | | 0/28 | 0/28 | 0/28 |

Example 10

Evaluation of Cross-Reactivity of Anti-PS1 IgG Induced by PS1-rEPA in Humans Via Competition ELISA with SA 336PS and SA 336 Bacteria ELISA plates are coated with SE PS1 polysaccharide at optimum coating concentration overnight at room temperature. Plates are washed and blocked with BSA to prevent the non-specific binding of antibodies. The inhibitor is 2-fold serially diluted starting from 200 µg PS/mL (SE PS1 or SA 336PS) or ABS$_{650}$=0.5 of the suspension of bacteria (SE PS1 prototype or SA 336 prototype). The 10 consecutive dilutions of inhibitor are added at 50 µL/well from well #2 through well#12 of one row on ELISA plate. To the well#1 of the same row, 50 µL of buffer is added, so this well does not contain inhibitor. Then, 50 µL/well of the human antiserum diluted to the concentration that is 2-fold higher than that that gives OD$_{450}$~1.5 (in anti-PS1 IgG ELISA) are added in to each well from #1 through #12. The plates are incubated with mixing for 1 hour at 37° C. Plates are washed and 100 µL/well of the goat anti-human peroxidase-labeled IgG (g) at the optimum working concentration is added. Plates are incubated for 1 hour at 37° C., washed and loaded with 100 µL/well of TMB-/ H$_2$O$_2$ substrate. Following the 10-minute incubation at room temperature, enzyme reaction is stopped by adding 100 µL/well of 1 M phosphoric acid. Absorbance is measured at 450 nm by means of the 96-well ELISA plate reader. The concentration of inhibitor that causes 50% reduction of anti-PS1 IgG is calculated from the inhibition curves via Prism-Graph.

Results from competition ELISA of seven human sera of vaccinees that received PS1-rEPA conjugate vaccine are presented in Table 8. All tested antisera were positive for anti-PS1 seroconversion (there was at least 4-fold increase in anti PS1 IgG compared to pre-vaccination level). Results show that anti-PS1 IgG induced by PS1-rEPA can be inhibited not only with PS1 (the polysaccharide used to prepare conjugate vaccine) but also with 336PS, which is the polysaccharide isolated from Staphylococcus aureus. Moreover, by competition ELISA with whole bacteria, it was shown that antibodies induced with PS1-conjugate vaccine in humans recognize not only homologous S. epidermidis 956 bacterial strain, but also heterologous S. aureus type 336 bacteria which suggests that PS1-conjugate antibodies could protect against Type 336 infections.

TABLE 8

Reduction in Anti-PS1 IgG by Inhibitor

| | Concentration of inhibitor causing 50% reduction of anti-PS1 IgG | | | |
|---|---|---|---|---|
| Sera from | Inhibitor (polysaccharide or suspension of bacteria) | | | |
| vaccinees receiving PS1-rEPA | SE PS1 (µg/mL) | SA 336PS (µg/mL) | SE strain 956 ABS (650 nm)* | SA type 336 prototype ABS (650 nm)* |
| 1 | 12.3 | 2.6 | 0.031 | 0.020 |
| 2 | 2.7 | 3.1 | 0.022 | 0.0075 |
| 3 | 4.5 | 7.6 | 0.022 | 0.0081 |
| 4 | 7.8 | >100 | 0.093 | 0.13 |
| 5 | 4.9 | 9.8 | 0.053 | 0.016 |
| 6 | 7.2 | >100 | 0.20 | >0.25 |
| 7 | 5.6 | 8.9 | 0.037 | 0.059 |

*Concentration of whole bacteria is represented here as absorbance at 650 nm Suspension of SE strain 956 or SA type 336 of ABS$_{650}$ = 0.25 contains 6 × 10$^7$ CFU/mL Example 11

Reactivity of Coagulase-negative and Coagulase-Positive Staphylococcal Species with PS1 Polyclonal Antibodies Using Slide Agglutination Staphylococcal isolates were plated on Columbia broth supplemented with 4% NaCl or modified Columbia media and grown overnight at 37° C. Cells were suspended in PBS and qualitatively tested for reactivity with PS1 rabbit polyclonal antibodies using a slide agglutination test. The reactivities were qualitatively scored (Table 9). Positive agglutination was observed with all isolates testing, demonstrating that antibodies to PS1 cross-react with a variety of coagulase-negative Staphylococci as well as S. aureus, a coagulase-positive strain.

TABLE 9

Reactivity of Staphylococcal Species using PS1-Conjugate Antibodies in Slide Agglutination.

| Isolate Type | Overall Reactivity in Slide Agglutination |
|---|---|
| S. epidermidis (Coagulase-negative) | majority are ++/+++ |
| S. hominus (Coagulase-negative) | weak/+ |
| S. haemolyticus (Coagulase-negative) | variable from (−) to +++ |
| S. capitis (Coagulase-negative) | variable from (−) to +++ |
| S. cohni (Coagulase-negative) | weak/+ |
| S. aureus (Coagulase-positive) | weak to +++ |

Thus, a method of preventing or treating bacterial infection in an individual has been described according to the present invention. Many modifications and variations may be made to the techniques and structures described and illustrated herein without departing from the spirit and scope of the invention. Accordingly, it should be understood that the methods described herein are illustrative only and are not limiting upon the scope of the invention.

What is claimed is:

1. A method for reducing the incidence of *Staphylococcus aureus* bacteremia in a patient in a population of patients at risk for infection by *Staphylococcus* comprising administering to a patient in the population a composition comprising a conjugate of an isolated *S. epidermidis* antigen with an immunocarrier, wherein the antigen binds with antibodies to *S. epidermidis* deposited under ATCC 55254, wherein the conjugate of the isolated *S. epidermidis* antigen produces antibodies that protect against a species or type of *Staphylococcus* other than *S. epidermidis* deposited under ATCC 55254, and wherein the antigen comprises a 1,3-poly(glycerol phosphate) polymer chain and N-acetyl-glucosamine residues attached to the 2-position of the glycerol.

2. A method for reducing the incidence of *Staphylococcus aureus* bacteremia in a patient in a population of patients at risk for infection by *Staphylococcus aureus*, comprising administering to a patient in said population a composition comprising a conjugate of an immunocarrier and an isolated *S. epidermidis* antigen that contains a 1,3-poly(glycerol phosphate) polymer chain and N-acetyl-glucosamine residues attached to the 2-position of the glycerol, wherein the antigen binds with antibodies to *S. epidermidis* deposited under ATCC 55254, wherein the isolated *S. epidermidis* antigen produces antibodies that protect against *S. aureus*, and wherein the antigen comprises a 1,3-poly(glycerol phosphate) polymer chain and N-acetyl-glucosamine residues attached to the 2-position of the glycerol.

3. A method according to claim 1, wherein said population of patients is at risk for infection by both coagulase-negative *Staphylococcus* and coagulase-positive *Staphylococcus aureus*.

4. A method according to claim 1, wherein said immunocarrier is a T-cell dependent immunogen.

5. A method according to claim 1, wherein said immunocarrier is a polypeptide or protein.

6. A method according to claim 1, wherein said antigen reacts with whole cell antisera to the *S. epidermidis* strain ATCC 55254 in a double immunodiffusion assay to produce a single precipitin band.

7. A method according to claim 6, wherein antiserum produced in response to said antigen is not reactive with 1,3-poly(glycerol phosphate) teichoic acids or with lipoteichoic acids which contain N-acetyl-glucosamine.

8. A method according to claim 1, wherein said antigen reacts with whole cell antisera to the *S. epidermidis* strain ATCC 55254 in a double immunodiffusion assay to produce a single precipitin band.

9. A method according to claim 8, wherein antiserum produced in response to said antigen is not reactive with 1,3-poly(glycerol phosphate) teichoic acids or with lipoteichoic acids which contain N-acetyl-glucosamine.

10. A method according to claim 1, wherein said immunocarrier is *Pseudomonas aeruginosa* exotoxin A.

11. A method according to claim 2, wherein said immunocarrier is *Pseudomonas aeruginosa* exotoxin A.

* * * * *